United States Patent [19]
Berke

[11] Patent Number: 5,976,173
[45] Date of Patent: Nov. 2, 1999

[54] NOSEFORM, COVER AND RESET-STRUCTURE AND METHOD

[76] Inventor: Joseph J. Berke, 2063 Long Lake Shore, West Bloomfield, Mich. 48033

[21] Appl. No.: 08/699,047

[22] Filed: Aug. 21, 1996

[51] Int. Cl.⁶ .................................................. A61F 5/08
[52] U.S. Cl. ................................ 606/204.45; 128/858
[58] Field of Search .................. 606/204.45, 205.25, 606/204.15; 128/858, 866

[56] References Cited

U.S. PATENT DOCUMENTS

| | | |
|---|---|---|
| 1,034,123 | 7/1912 | Knowlson . |
| 1,043,924 | 11/1912 | Gottlieb . |
| 1,232,956 | 7/1917 | Mooney . |
| 1,950,839 | 3/1934 | Chirila . |
| 2,335,936 | 12/1943 | Hanlon . |
| 2,515,756 | 7/1950 | Bove . |
| 3,594,813 | 7/1971 | Sanderson ............................. 128/858 |
| 3,710,799 | 1/1973 | Caballero . |
| 3,835,848 | 9/1974 | Berner ................................ 606/204.45 |
| 4,201,217 | 5/1980 | Slater . |
| 4,402,314 | 9/1983 | Goode . |
| 4,414,977 | 11/1983 | Rezakhany . |
| 4,576,168 | 3/1986 | Jalowayski . |
| 4,759,365 | 7/1988 | Askinazy . |
| 5,022,389 | 6/1991 | Brennan ................................ 128/858 |
| 5,669,377 | 9/1997 | Fenn ................................. 606/204.45 |

Primary Examiner—Michael Buiz
Assistant Examiner—Kevin Truong

[57] ABSTRACT

A cover and noseform is disclosed for protecting, dilating and maintaining dilation of the nose as well as aligning the nasal passages with the nares of the nose to increase the efficiency of breathing and prevent problems such as snoring. The noseform is applied to cover at least a portion of the nose and causes the end or apex of the nose to be lifted in a direction aligned with the nose and toward the forehead of the person to align the nares and nasal passages of the nose. The noseform includes a first portion adhered to the nose, a second portion adhered to the nose distal from the first portion and a means for moving the second portion toward the first portion to lift the end of the nose toward the glabella or forehead region as well as covering the nose of the wearer. The noseform also includes a rest to prevent a pair of glasses from slipping down the nose and constricting the nasal passages. Furthermore, the noseform of the present invention is designed to be decorated and altered to achieve differing aesthetic appearances including a passage therethrough for creating a sun-tattoo as well as extensions over the forehead.

15 Claims, 4 Drawing Sheets

NOSEFORM, COVER AND RESET-STRUCTURE AND METHOD

BACKGROUND OF THE INVENTION

1. Field of the invention

The present invention generally relates to an apparatus and method for altering the appearance and performance of the nose. The present invention further relates to a means of elevating the nose from apex to root and changing its shape thereby dilating the nasal passages. The noseform and nasal passage dilator apparatus of the present invention may be designed to provide a protection of the nose and glabella from sun damage. The noseform provides an aid in breathing, increased respiratory efficiency and enhanced performance of physical activities. In another embodiment the noseform acts as a rest support for eyeglasses to prevent slippage which leads to nasal passage constriction from the glasses pressing the outside of the nose.

The noseform of the present invention allows styling opportunity—a wide variety of sizes and shapes can be imagined. The apparatus may also cover the glabella and other parts of the forehead for additional sun protection. The noseform may contain a cut-out to create a decorative "sun-tattoo".

2. Description of the Prior Art

It is well known that humans are most conscious of and constantly trying to improve their appearance. It is also well known that humans are also always trying to improve their health and performance. Many humans have significant problems with the nasal passages of their nose being constrictive thereby preventing easy and efficient breathing. A brief explanation of the anatomy, physiology and pathology of the nose will help to better understand the causes of the above mention problems and the need for this invention.

The human nose, located on the anterior middle portion of the head in the middle of the face, is sometimes compared to a three-sided pyramid with its internal skeleton referred to as the nasal pyramid. The base of the nose faces downward and surrounds the nares, commonly referred to as the nostrils, which open into the nasal cavities. The two nasal cavities are narrow above, wider below, and are separated by the nasal septum. The lower portions of the nasal cavities are referred to as the vestibules and are lined with a mucous membrane and provided with hairs for filtering debris.

The sides of the nose (or pyramid) meet in the middle of the nose along the dorsum nasi which extends from the root of the nose, continuous with the forehead, to the apex or tip of the nose. The lower portion of the side of the nose, which is typically flared, is referred to as the ala or wing. See FIG. 1 for a detail of the nose.

The nose further includes lateral nasal (or upper) cartilages which are unitary and continuous with each other and a septal cartilage, which extends backward and downward from the lateral nasal cartilages to articulate with the septum, and downward toward the apex of the nose. Greater alar (or lower) cartilages are located below the lateral nasal cartilages and laterally from the septal cartilage. The greater alar cartilages support their respective ala and form a lower part of the nasal structure. The middle and upper regions of the skin over the dorsum nasi including the lateral nasal cartilage and the septal cartilage is movable thus allowing the tip or apex of the nose to be lifted because the skin will not move over the apex of the nose.

Since the skin is movable over some regions of the nose, there are associated therewith known lines of tension of the skin. The known lines of tension of the skin are commonly referred to as Langer's lines, see FIG. 2. The lines of tension typically run in directions transverse to the direction in which the skin moves. With age the skin hypertrophies resulting in additional skin causing the nasal passages to become constricted or closed.

With the above information regarding the anatomy of the nose, some of the problems associated with the nose become more understandable. The most common problem associated with the nose is snoring. Other problems include a deviated septum and nasal polyps. Additionally, diseases such as Rhinophyma, benign lesions, collagen diseases, etc. alter nose anatomy and cause impingement upon the nasal passages. Altering the shape of the nose is known to affect these conditions. Furthermore, it is very well known that some people do not like the shape or size of their nose and spend large sums on expensive surgeries to alter the appearance of their nose.

Prior to the present invention attempts to use devices to dilate or more fully open nasal passages in humans and in animals have been described. Such devices claim to provide easier breathing and to help eliminate snoring. Occasionally, such devices are also used by athletes to help increase the amount of air intake and thereby increase the amount of air in the bloodstream to augment their physical performance and endurance.

An example of one type of prior art device is the insert device of U.S. Pat. No. 4,414,977, to Rezakhany, which discloses a nasal dilator adapted to be inserted into the nostril of the human nose to prevent the tissues of the ostium internum of the nose from contracting during breathing. Many devices similar to the Rezakhany reference disclose variations which prevent the nose from sagging and drooping or also dilate the nostrils to allow an increased flow of air through the nostrils. A representative group of these patents includes U.S. Patent No. 2,335,936, to Hanlon; U.S. Pat. No. 2,515,756, to Bove; U.S. Pat. No. 3,710,799, to Caballero; U.S. Pat. No. 1,232,956, to Mooney; U.S. Pat. No. 4,759,365, to Askinazy; and U.S. Pat. No. 4,576,168, to Jalowayski.

However, these types of insert devices are uncomfortable, cumbersome, expensive and potentially very dangerous. This is particularly true for an athlete engaged in a competition which is very fast paced, trauma prone or physical as are many sports today such as soccer, lacrosse, football, basketball and in particular ice hockey (especially when) struck in the nose.

Another class of devices for dilating a nasal passage is disclosed in U.S. Pat. No. 1,950,839, to Chirila, which discloses a pair of suction members which are applied to the outer skin surface of the nose over the septal cartilage between the dorsum nasi and the alac. The suction members stick to the skin of the nose and are biased outward to dilate the nasal passage to facilitate breathing. Similar to the Chirila device are U.S. Pat. No. 1,034,123, to Knowlson; U.S. Pat. No. 1,232, 956, to Mooney; U.S. Pat. No. 1,043, 924, to Gottlieb; and U.S. Pat. No. 4,201,217, to Slater, which all expand upon the idea of pulling or pushing the sides of the nose outward as a way of dilating the nasal passages.

However, the Chirila device and the others like it are also very bulky, cumbersome, ugly and potentially very dangerous when a blow to the nose occurs. Furthermore, the prior art proposed solutions have not conceived of possible uses and combinations which can be made with such devices.

Accordingly, in the prior art, dilation of the nasal passages of a human nose by stretching or pulling the outer sides of the nasal passage has been proposed. Also, the prior art requires large, unsightly devices for dilating the nasal passage and lacks a structure which is compact, ornamental and safe to use.

Despite the many attempts in the prior art, there is a failure of the known devices for nasal dilation to provide a structure which will prevent damage to the skin of the nose from environmental factors. Further, none of the known devices have a decorative appearance which may be selected by a user while improving ventilation and respiration by dilating the nostrils. In addition to the above, there is still a need to provide a noseform having a support and rest to prevent a pair of eyeglasses or sunglasses from slipping or sliding down the nose and constricting the air passages of the nose.

The elimination of problems associated with nasal passage constrictions such as snoring is a particular additional benefit of the present invention.

SUMMARY OF THE INVENTION

The present invention is novel in providing a decorative cover for the nose to prevent damage to the skin of the nose from environmental conditions such as the sun's rays, wind and airborne contaminants. Furthermore, the present invention is novel in providing a device and method for dilating the nares of the nose to prevent structures of the nose from collapsing, sagging and drooping during breathing.

More particularly, the present invention relates to an improved apparatus and method for achieving and maintaining dilation of the nasal passages of a human to increase breathing efficiency and prevent snoring. The apparatus is preferably designed to fix the end of the nose, following movement in a direction toward the glabella, to more accurately align the openings of the nares with the nasal passages and to prevent the septal cartilage and alae from moving inward while inhaling.

The present invention includes a first portion attached to the nose just below the glabella, a second portion attached below the bridge of the nose, and a mechanism, interconnecting the first and second portions, for moving the second portion toward the first portion such that the tip of the nose remains fixed toward the glabella with the nasal passages dilated.

The present invention includes a method for dilating the nasal passages of the nose by moving the end of the nose toward the glabella to dilate the nasal passages and fixing the position of the end of the nose moved toward the glabella by using the device of the present invention. The method of the present invention includes first moving the nose toward the glabella and then fixing of a first portion of the device and then fixing of a second portion of the device. Alternatively, the method of the present invention includes first the fixing or attaching of the first portion of the device of the present invention to a point just below the glabella, next, the moving of the end of the nose toward the glabella, and then the fixing or attaching of the second portion of the device to the nose at a point below the bridge of the nose to fix the movement of the end of the nose and thereby dilate the nasal passages to improve breathing efficiency.

Thus, it is a primary object of the present invention to provide a device for improving the breathing through the nasal passages of a human by moving the apex of the nose in a direction toward the glabella thereby changing the size and shape of the nose and dilating the nares.

It is a further object of the present invention to provide a device for covering the nose of a human using a decorative object adherent to the skin of the nose.

It is yet another object of the present invention to provide an apparatus which prevents the soft tissue and cartilage of the nose from closing the aperture while a person inhales.

It is a further object of the present invention to provide an apparatus which while preventing the soft tissue and cartilage of the nose from being constricted when a person inhales can also function as a support and rest for a pair of eyeglasses or sunglasses to prevent them from slipping down the person's nose and constricting the nasal passages which reduces breathing efficiency.

It is yet another object of the present invention to provide an apparatus which prevents the soft tissue and cartilage of the nose from being drawn in while a person inhales which is easy to use, less expensive and more safe than known prior art designs.

Other objects and advantages of the present invention will become apparent in the following detailed description of the invention with reference being made to the drawings. First, a brief description of the drawings will follow.

DETAILED DESCRIPTION OF THE PREFERRED EMBODIMENT

With general reference to FIGS. 1 through 10, and particular reference to FIGS. 4 through 7, a noseform, generally designated by the numeral 10 in the drawings, (noseforms of alternative embodiments are shown in the Figures with all similar items being numbered the same with a multiple of 100 added thereto), of the present invention is shown for covering and altering the nose region of a human.

Figures 1, 2:
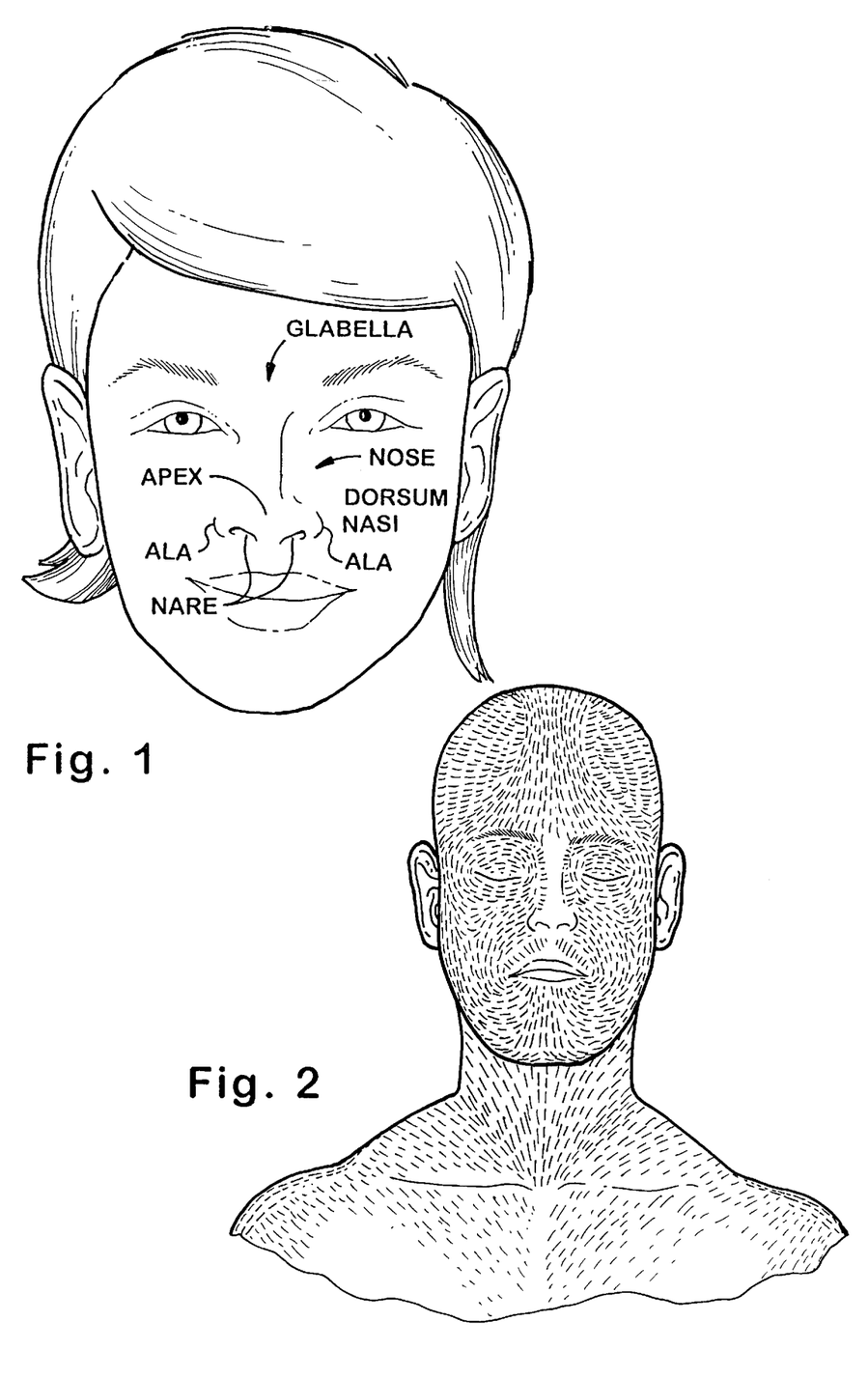
FIG. 1 is a front view of a human face detailing the external composition and features of the human nose.
FIG. 2 is a front view of a human showing the skin over the human nose and detailing the Langer's lines of the face and nose.

FIG. 1 shows the external parts of the human nose including names of the detailed parts. A detailed explanation of the external nose is set forth above. The nose is covered by skin which is movable in certain directions. The skin falls along certain lines (historically referred to "Langer's" lines) which identify how the skin is movable. FIG. 2 shows the Langer's lines for the face of a human. It should be noted that the lines along the nose run approximately transverse to the aligned direction of the nose along approximately the center of the face. Thus, the skin of the nose is most easily moved essentially vertically along the direction of the nose (this is also along the aligned direction of the dorsum nasi).

Figure 3:
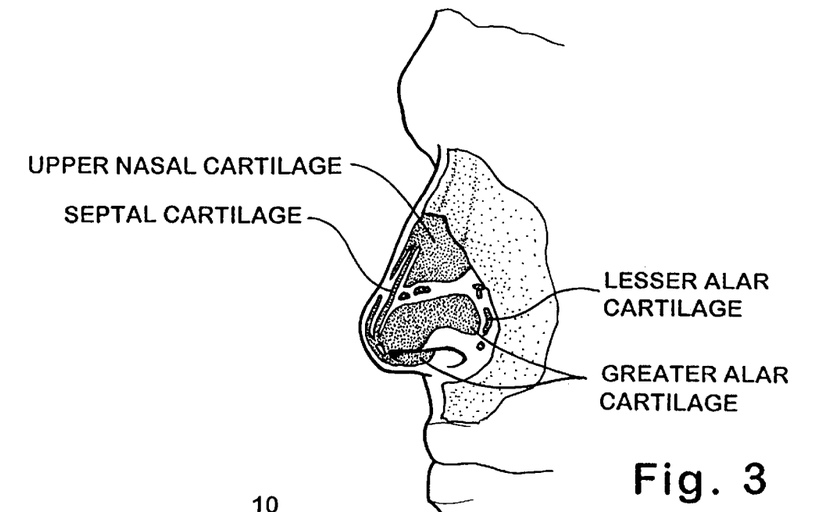
FIG. 3 is a side view detailing the internal composition of the human nose.

FIG. 3 shows the internal features of the nose including the cartilages and bones of the nose. As discussed above, the skin is more easily movable over the bone and upper parts of the nose, whereas the skin is less movable over the lower region of the nose including the apex and lower alar cartilage. Thus, when the lower part of the nose, or the apex, is moved toward the upper part of the nose, or toward the forehead or glabella region, the nares of the nose are aligned with the nasal passages resulting in easier, more efficient breathing.

Figure 4:
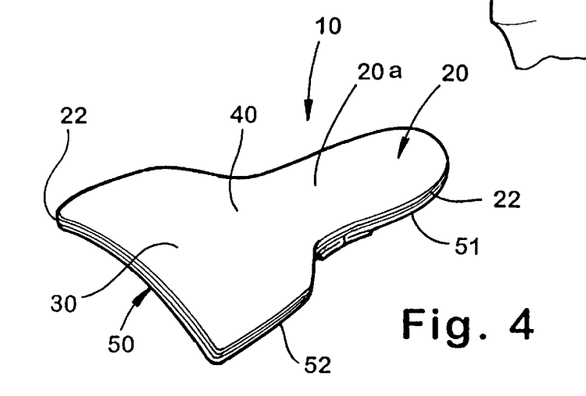
FIG. 4 is a perspective view illustrating a noseform device according to a preferred embodiment of the present invention.

FIG. 4 shows the noseform 10 according to the present invention which is designed to cover the nose and hold the apex of the nose in a position moved toward the glabella. The noseform 10 of the preferred embodiment shown in FIGS. 4 through 7 is shown as a unitary piece. However, as shown in the alternative embodiments, it is possible to assemble the pieces of the noseform 10 together to achieve the same outcome.

The noseform 10 of the preferred embodiment preferably includes a first portion 20 attached to the nose. It is preferable that the first portion 20 be attached along the dorsum nasi of the nose, however, it is possible to attach the first portion 20 along the side of the dorsum nasi near the bridge of the nose.

The noseform 10 of the preferred embodiment further includes a second portion 30 attached to the nose at a point between the first portion 20 and the apex of the nose. In the preferred embodiment, the second portion 30 is below the bridge of the nose and the first portion 20 is above the bridge of the nose. The noseform 10 further includes a flexible portion 40 interconnecting and biasing the first portion 20 toward the second portion 30 as more fully explained below.

The noseform 10 is preferably manufactured from a relatively thin flexible elastic material forming a substrate 10a. Known suitable substrates include plastic and cloth. The substrate 10a preferably has an adhesive backing 22 for adhering to the skin of the nose. In particular, it is preferable that the noseform 10 be made of a material which is pliable and can conform to the contour of differently shaped noses as well as porous to allow skin to breath and sweat to evaporate. An example of such a plastic or cloth is the type used to make adhesive strip bandages.

The noseform 10, also includes an adhesive cover 50 for use in packaging and shipping the noseform 10. In particular, the cover 50 is cut into a first cover portion 51 and a second cover portion 52 which can be easily peeled from the adhesive layer 22 when a user wishes to apply the noseform 10. Thus, the cover 50 is similar to adhesive covers used on adhesive strip bandages.

Figure 9:
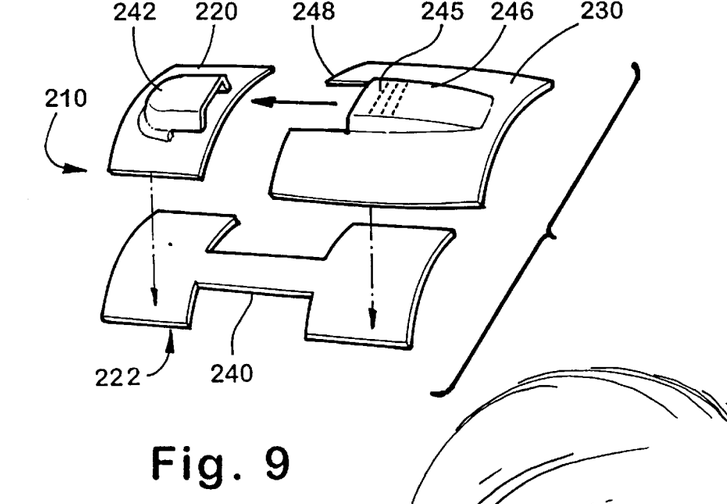
FIG. 9 is a perspective view of a noseform device according to an alternative embodiment of the present invention.

Since the first portion 20 is preferably positioned along the dorsum nasi of the nose, if the first portion 20 has any appreciable width, it must bend transversely to the direction of the dorsum nasi in order to conform to the curvature of the nose. Furthermore, it is possible to have the first portion 20 cover only a small portion of the nose, such as the first portion 20 shown in FIG. 4, or to have a first portion 220 as shown in FIG. 9 which covers a more substantial portion of the nose, or to even have a first portion 320 which covers the entire nose and extends onto the forehead as shown in the alternative embodiment of FIG. 10.

The adhesive backing 22 of the first portion 20 (as well as the alternative embodiments) is preferably similar to the adhesive backing used on adhesive bandages so it will stick and hold to the skin of the human nose, but will not cause pain or problems when the noseform 10 is removed from the nose. The adhesive 22 is preferably hypo-allergenic and unabrasive. Furthermore, the bonding strength of the adhesive 22 is calculated to provide adequate adherence of the noseform 10 to the skin of the nose and withstand the biasing force of the flexible portion 40 forcing the second portion 30 toward the first portion 20 without causing either portion to become disconnected from the skin.

While the present invention has been shown as consisting of the substrate 10 a to which the adhesive layer 22 is connected, it should be understood that it would be equivalent to put the adhesive on a member which is then attached to the substrate 10a.

Figure 5:
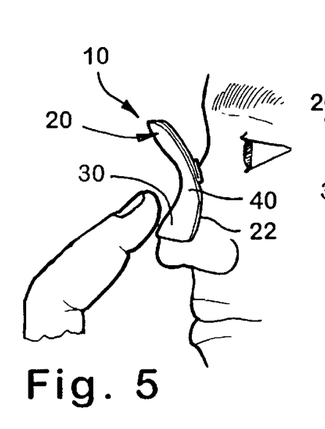
FIG. 5 is a side view of the noseform device according to the embodiment of FIG. 4 showing the application of the noseform and elevation of the human nose.
Figure 6:
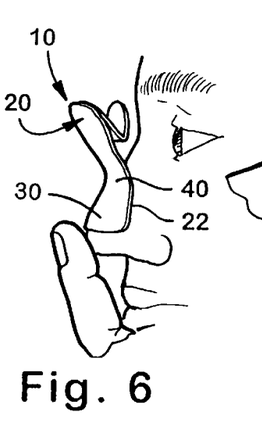
FIG. 6 is a side view of the noseform device according to the embodiment of FIG. 5 showing the application of the noseform to the human nose at a later step than FIG. 5.
Figure 7:
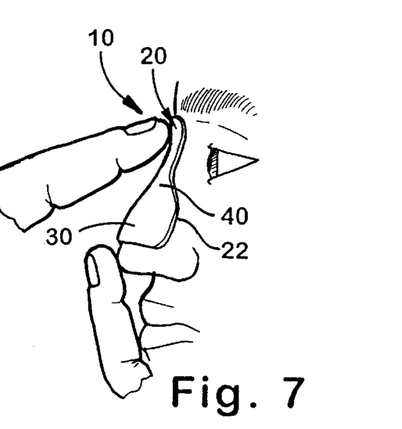
FIG. 7 is a side view of the noseform device according to the embodiment of FIG. 5 showing the application of the noseform to the human nose at a later step than FIG. 6.

The noseform 10 of FIG. 4 is applied to the nose using a process intended to cover and dilate the nasal passages of the nose as shown in picture sequence form in FIGS. 5 through 7. The noseform 10 has its second cover portion 52 peeled off and the adhesive portion 22 is applied to the lower end of the nose as shown in FIG. 5. Next, the wearer pushes the apex of the nose in a direction toward the wearer's forehead or glabella causing the nares to align with the nasal passages causing them to dilate as shown in FIG. 6. The first cover portion 51 is peeled off of the first portion 20 at any time and the first portion 20 is then attached to the nose at a point around the bridge of the nose, or just below the glabella. Thus, the noseform 10 and in particular, the flexible portion 40, causes the end of the nose to remain lifted.

Since the substrate 10a is elastic and its ends have been stretched apart and attached to separate points along the dorsum nasi, the substrate 10a will contract and bias the ends toward one another, i.e. the flexible portion 40, and the nose will remain lifted. This results in the nostrils of the nose being dilated and maintained in dilatation as described above. Thus, the noseform 10 covers the nose and dilates the nostrils in a very simple and efficient manner according to the present invention.

Figure 8:
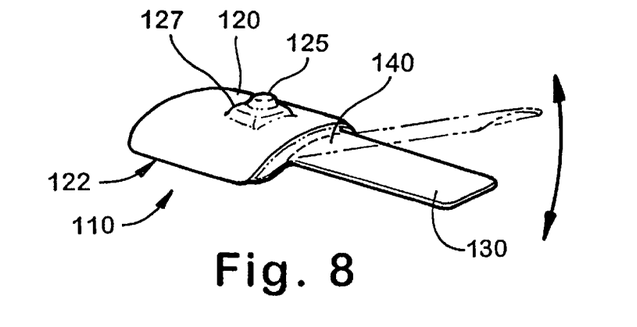
FIG. 8 is a perspective view of a noseform device according to a second alternative embodiment including an eyeglass support according to the present invention.

In the alternative embodiment shown in FIG. 8, there is shown a two piece noseform 110 including a first portion 120 and a second portion 130. In the present alternative embodiment, the first and second portions are preferably made of a material similar to that of the first embodiment of FIG. 4. However, the first portion 120 now includes a raised portion 125 located on the first portion 120. The raised portion 125 creates a rest or dwell 127 next thereto where the glasses stay once properly positioned. When a wearer has the noseform 110 properly positioned on the nose, the dwell is proximately located the bridge of the nose of the wearer and acts as a support for a pair of glasses to prevent the glasses from slipping down the wearer's nose and constricting the nasal alae.

To properly place the dwell 127 in the correct spot for the wearer, the noseform 110 preferably is applied to the nose by first attaching the first portion 120, then lifting the nose and then stretching and attaching the second portion 130. Thus, the flexible portion 140 creates a biasing force causing the end of the nose to continue to be lifted as in the case of the noseform 10.

In the alternative embodiment of FIG. 9, there is shown a noseform 210 including a first portion 220 a second portion 230 and a flexible portion 240. However, in the present embodiment, the flexible portion 240 and the adhesive layer 222 are attached to the first and second portions which are now preferably made of a plastic material having a higher stiffness. The flexible portion 240 is designed to be attached to the first and second portions 220 and 230, respectively, such that the portions overlap. The noseform 210 of the present invention further includes an indexing means for adjusting the distance between the first portion 220 and the second portion 230.

The indexing means includes a first projection 242 extending from the first portion 220 and a series of stops 245 located on the inside of a second projection 246 on the second portion 230. The first projection 242 is received within a slot 248 in the second portion 230. The first projection 242 and the stops 245 interact to adjust the amount of overlap between the first portion 220 and the second portion 230.

Thus, the wearer first applies the first portion 220 to the nose and then lifts the nose as previously discussed. Next, the wearer stretches the flexible portion 240 to create a biasing force therein and then attaches the second portion 230 to the nose distal from the first portion 220. The wearer can precisely adjust the distance between the first and second portions by selecting a particular stop 245 for the first projection 242 to rest against.

Figure 10:
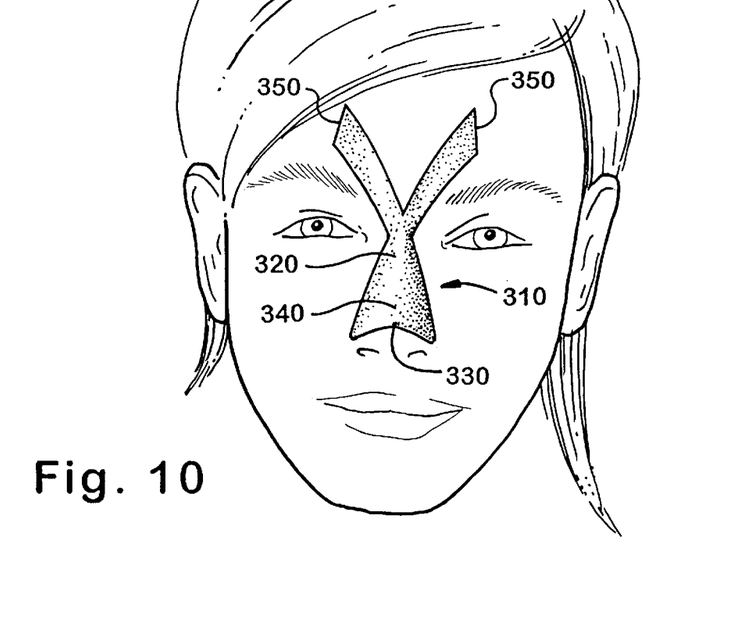
FIG. 10 is a front view of a noseform device having a forehead extension a human face as a third alternative embodiment according to the present invention.

In a third alternative embodiment shown in FIG. 10, there is shown a noseform 310, including a first portion 320, a second portion 330 and a flexible portion 340 similar to the noseform 10 as previously discussed. The noseform 310 is intended to be very decorative and includes a pair of extensions 350 which extend over the glabella and forehead of the wearer. The extensions 350 also include the adhesive material on their skin side to adhere the extensions to the wearer's skin to provide added adhesion and a unique decorative effect.

Figure 11:
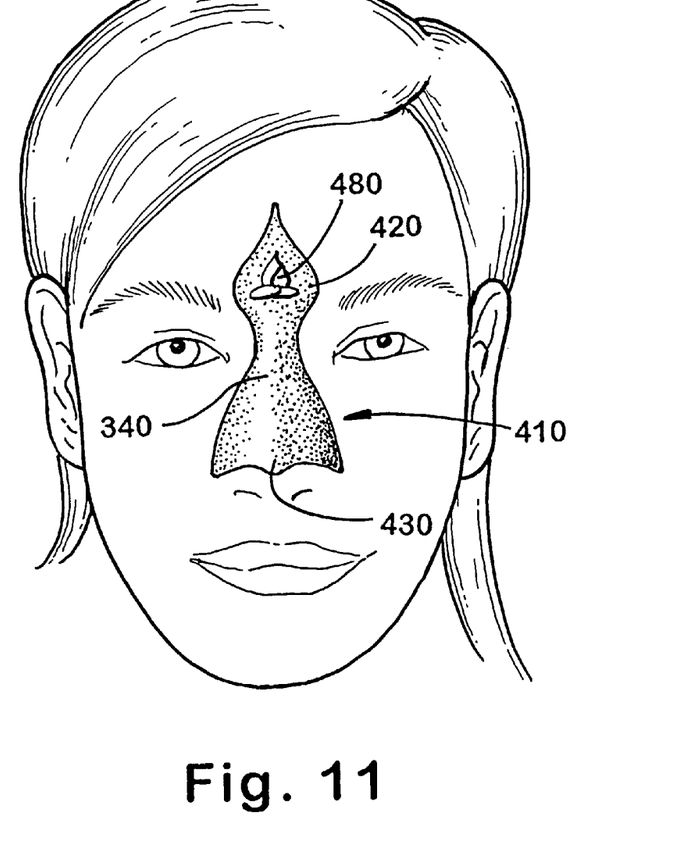
FIG. 11 is a front view of a decorative noseform on a human face of a fourth alternative embodiment according to the present invention including a sun-tattoo.

In FIG. 11 there is shown a noseform 410 according to a further alternative of the present invention. As can be seen from the noseform 410 of the present invention it is possible to make the noseform 410 very decorative in addition to being functional. The noseform 410 of the present embodiment is similar to the noseform 10, in that it is made of an elastic substrate and has a first portion 420, a second portion 430 and a flexible portion 440 for biasing the first portion 420 relative to the second portion 430 and vice versa to lift and maintain lifted the end of the nose. Furthermore the noseform 410 is adhesively attached to the skin of the wearer.

The noseform 410 further includes a hole or passage 480 through the substrate in the first portion 420. In the present embodiment, the hole 480 is spade-shaped, but it is possible to have any desired shape for the hole 480. Furthermore, the hole 480 may be placed anywhere in the noseform 410. Similarly, the noseform 410 can be shaped in different configurations to achieve a reverse sun-tattoo. Thus, the wearer has the noseform 410 positioned over the nose and is then exposed to sunlight or tanning rays. Since the noseform 410 is made of a nonlight-transitive material, the hole 480 allows the sunlight to tan the skin of the wearer through the hole 480. Once the noseform 410 is removed the skin located in the hole 480 will be tan and the skin located under the noseform 410 will not be tan, thus creating a sun-tattoo.

Figure 12:
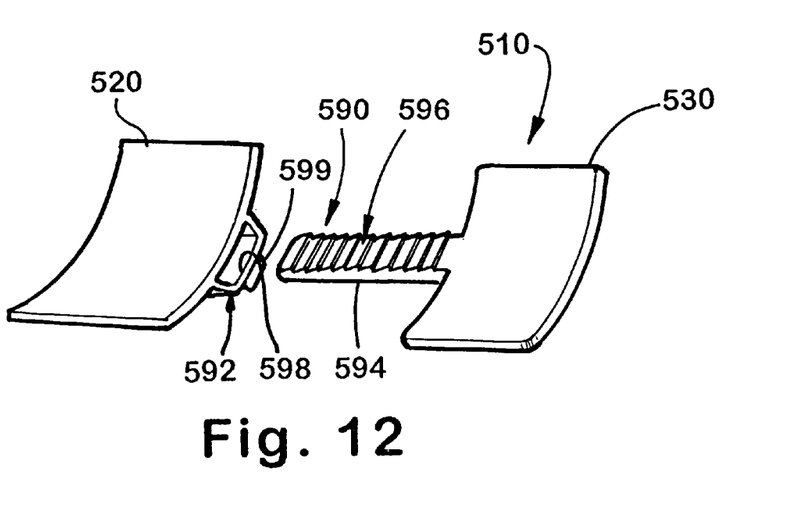
FIG. 12 is a perspective view of a noseform of a fifth alternative embodiment according to the present invention showing a squeeze clamp for maintaining the lift of the noseform.

In a fifth alternative embodiment of the present invention, shown in FIG. 12, a two piece noseform 510 is disclosed including a squeeze clamp connector 590. The noseform 510 is held to the skin of the wearer using an adhesive, as in the previous embodiments. The noseform 510 includes a first member, portion or substrate 520 and a second member, portion or substrate 530, which may or may not be separate from the first substrate 520. The first and second substrates are connected together using the connector 590. The first and second substrates can be any member and made of any material appropriate for the present purpose, as described above, including all types of cloths, plastics, metals, alloys or even ceramics without departing from the scope of the present invention. The first and second substrates of the noseform 510 are preferably made from a lightweight, pliable plastic having an adhesive layer for connecting to the skin of the wearer, as described above.

The connector 590 includes a receptacle 592 attached to the first substrate 520 and a extended or projecting member 594 attached to the second substrate 530. The extended member 594 includes a row of teeth 596 which interact and abut against a latch 598 located in the receptacle attached to the first substrate 520 to complete the connection. A release 599 is connected to the latch 598 for releasing the latch 598 from the row of teeth 596 of the extended member 594.

Thus, the wearer first connects the first and second substrates 520 and 530, respectively, at first position which will allow further sufficient movement therebetween. Next, the noseform 510 is applied to the skin of the nose in a direction aligned with the dorsum nasi and at a position allowing for the end of the nose to be lifted as previously described. Once the noseform 510 is applied, the wearer then pushes the second substrate 530 toward the first substrate 520 which causes the end of the nose to lift toward the glabella thereby dilating and aligning the nares with the nasal passages and improving breathing efficiency as well as preventing inefficient breathing problems such as snoring.

It should be understood that the row of teeth 596 of the extended member 594 are ramped in the insertion direction to allow easy insertion of the extended member 594 into the receptacle 592 and are not ramped in the opposite direction to prevent the extended member 594 from being removed from the receptacle 592 without using the release 599.

While the invention has been described in terms of a preferred embodiment with reference to several alternative embodiments, it should be apparent to one skilled in the art that variants and substitutes to the elements of the above described invention can be adopted by one skilled in the art without departing from the present invention. Accordingly, the scope of the invention is to be limited only by the following claims.

What is claimed is:

1. An apparatus for covering a nose and improving breathing efficiency, the nose located next to a glabella and having an apex, a dorsum nasi and nasal passages, said apparatus comprising:

means for moving the apex of the nose is a direction substantially aligned with the dorsum nasi and toward the glabella;

means for attaching said moving means to the nose, said attaching means connected to said moving means, said attaching means having a first end and a second end wherein said attaching means is located below the glabella; and means for holding the apex of the nose in position once moved by the moving means;

whereby when the apex of the nose is moved toward the glabella, the nasal passages are dilated and aligned to allow more efficient breathing.

2. The apparatus of claim 1 further comprising:
a first portion connected to a first portion of the nose and positioned with respect to the glabella;
a second portion having a portion connected to the nose more distal from the glabella than the first portion; and
a living hinge connected between the first portion and the second portion to move the second portion with respect to the first portion to move the apex of the nose toward the glabella.

3. An apparatus for dilating the nasal passages of a nose on a human face having a glabella, the apparatus comprising:
a flexible elastic substrate for covering the nose;
a first portion of the substrate attached to the nose;
a second portion of the substrate attached to the nose at a point distal from the first portion of the substrate and at a point below the glabella; and
a flexible portion located between the first portion and the second portion, said flexible portion biasing said first portion of the flexible elastic subtrate toward the second portion of the flexible elastic substrate.

4. An apparatus for dilating the nasal passages of a nose on a human face, the apparatus comprising a first extension connected to said apparatus and defining a dwell for supporting a pair of glasses to prevent slippage resulting in constriction of the alae.

5. An apparatus for dilating the nasal passages of a nose on a human face, the apparatus comprising:
a flexible elastic substrate for covering the nose;
a first portion of the substrate attached to the nose;
a second portion of the substrate attached to the nose at a point distal from the first portion of the substrate;
a flexible portion located between the first portion and the second portion;
a first extension connected to the first portion; and
a second extension connected to the second portion, the second extension having a plurality of stops located for interacting with the first extension of the first portion for adjusting the distance between the first portion and the second portion to adjust the amount the apex is lifted from its rest position.

6. A method of covering a nose and dilating the nostrils of the nose located proximate a glabella, the method comprising the steps of:
attaching a first end of the elastic substrate to a first point along the dorsum nasi of the nose;
stretching a first end of an elastic substrate in a direction aligned with the dorsum nasi of the nose to store energy in the elastic substrate; and
attaching the second end of the stretched elastic substrate to a second point distal from the first point and below the glabella, along the dorsum nasi of the nose;
whereby the apex of the nose is lifted and the nostrils of the nose are dilated.

7. An apparatus for covering a nose of a human, the apparatus comprising:
a first cover portion having a first side facing the nose, the first cover portion positioned over a portion of the nose;
an adhesive applied to the first side of the first cover portion for adhering the first cover portion to the nose;
a second cover portion separate from the first cover portion, the second cover portion manufactured separately from the first cover portion, the second cover portion having a first side facing the nose, the second cover portion positioned with respect to the first cover portion;
an adhesive applied to the first side of the second cover portion for adhering the second cover portion to the nose; and
means for biasing the second cover portion toward the first cover portion such that the apex of the nose is lifted.

8. A method of dilating the nares of a human nose on a face having a glabella, the method including using an apparatus for dilating the nares of the nose, said method comprising the steps of:
moving the apex of the nose in a direction substantially aligned with the direction of the dorsum nasi of the human nose;
attaching a first portion of said apparatus to a first portion of the nose proximal the apex of the nose;
attaching a second portion of said apparatus to a second portion of the nose distal the apex of the nose from the first portion and below the glabella; and
interconnecting the first portion to the second portion of said apparatus with a means for biasing the first portion toward the second portion such that the apex of the nose is lifted.

9. A device for supporting a pair of eyeglasses worn by a human, the device comprising:
a first portion having a first side facing the nose of the human, the first portion located on the nose of the human;
an adhesive applied to the first side of the first portion for securing the first portion to the nose; and
a support portion connected to the first portion, the support portion for engaging the eyeglasses to prevent the eyeglasses from slipping.

10. An apparatus for dilating the nasal passages of a nose on a human face by moving the end of the nose in a direction toward the glabella, the apparatus comprising:
a first substrate attached to and covering a first portion of the nose;
a second substrate separate from the first substrate, the second substrate attached to and covering a second portion of the nose at a point distal from the first substrate and below the glabella; and
a means for connecting the first substrate to the second substrate, the connecting means fixing the position of the second substrate with respect to the first substrate to maintain the end of the nose in a lifted position and the nostrils of the nose dilated.

11. An apparatus for dilating the nasal passages of a nose on a human face, having a glabella, by moving the end of the nose in a direction toward the glabella, the apparatus comprising:
a first substrate attached to and covering a first portion of the nose;
a second substrate attached to and covering a second portion of the nose at a point distal from the first substrate; and
a means for connecting the first substrate to the second substrate, the connecting means fixing the position of the second substrate with respect to the first substrate to maintain the end of the nose in a lifted position and the nostrils of the nose dilated; and wherein the connecting means comprises:

a receptacle connected to the first substrate, the receptacle having a latch; and an extension member connected to the second substrate and having a row of teeth, the extension member received in the receptacle of the first substrate such that the row of teeth of the extension member overlap with the latch of the receptacle.

12. The apparatus according to claim 11 further comprising a release connected to the latch for releasing the latch from the row of teeth to allow the extension member to be withdrawn from the receptacle.

13. A method of dilating the nostrils of a person by lifting the end of the nose using a noseform including a first substrate, a second substrate, a connector including a receptacle having a latch attached to the first substrate and an extended member having a row of teeth attached to the second substrate, the method comprising the steps of:

connecting the first and second substrates by inserting the extended member into the receptacle to a first position;

applying the noseform to the skin of the nose at a position allowing for the end of the nose to be lifted; and moving the second substrate toward the first substrate to cause the end of the nose to lift toward the glabella causing the extended member's row of teeth to insert further into the receptacle;

whereby the nostrils are dilated and aligned with the nasal passages of the nose.

14. An apparatus for dilating the nasal passages of a nose on a human face, the apparatus comprising:

a flexible elastic substrate for covering the nose;

a first portion of the flexible elastic substrate attached to the nose;

a second portion of the flexible elastic substrate attached to the nose at a point distal from the first portion of the flexible elastic substrate;

a flexible portion for biasing the first portion toward the second portion, the flexible portion located between the first portion and the second portion; and a passage located in the flexible elastic substrate for creating a sun-tattoo on the face.

15. A method for dilating the nares of a human nose, the method comprising the steps of:

moving the apex of the nose in a direction substantially aligned with the direction of the dorsum nasi of the human nose;

attaching a first portion of an apparatus, for dilating the nose, at a point above the bridge of the nose prior to the step of moving the apex of the nose in a direction substantially aligned with the direction of the dorsum nasi of the human nose; and attaching a second portion of the apparatus at a point below the bridge of the nose after the step of moving the apex of the nose in a direction substantially aligned with the direction of the dorsum nasi of the human nose;

whereby the apparatus maintains the apex of the nose in a lifted position and maintains dilation of the nares.

* * * * *